(12) United States Patent
Minch et al.

(10) Patent No.: US 8,492,542 B2
(45) Date of Patent: Jul. 23, 2013

(54) METHOD FOR PRODUCING BICYCLIC GUANIDINES BY USE OF A CYCLIC THIOUREA

(75) Inventors: Britt A. Minch, Tarentum, PA (US); Charles R. Hickenboth, Cranberry Township, PA (US); Richard F. Karabin, Ruffs Dale, PA (US); Steven R. Zawacky, Pittsburgh, PA (US); Thomas R. Hockswender, Gibsonia, PA (US); Gregory J. McCollum, Gibsonia, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 1195 days.

(21) Appl. No.: 12/120,725

(22) Filed: May 15, 2008

(65) Prior Publication Data

US 2009/0286978 A1 Nov. 19, 2009

(51) Int. Cl.
*C07D 487/04* (2006.01)
*C07D 239/10* (2006.01)
*C07D 235/02* (2006.01)
*C07D 233/44* (2006.01)

(52) U.S. Cl.
USPC ...... 544/279; 544/315; 548/303.1; 548/325.1

(58) Field of Classification Search
USPC ............. 544/279, 315; 514/303.1; 548/303.1, 548/325.1
See application file for complete search history.

(56) References Cited

U.S. PATENT DOCUMENTS 4,797,487 A 1/1989 A'Court

OTHER PUBLICATIONS

Cotton et al., "Homologues of the Easily Ionized Compound Mo2(hpp)4 Containing Smaller Bicyclic Guanidinates", Inorganic Chemistry, vol. 45, No. 14, 2006 pp. 5493-5500.
Schmidtchen, "Synthese Symmertrisch Substituierter Bicyclischer Guanidine", Chemische Berichte, vol. 113, No. 6, 1980, pp. 2175-2182.

*Primary Examiner* — Venkataraman Balasubramanian
(74) *Attorney, Agent, or Firm* — Diane R. Meyers

(57) ABSTRACT

The present invention is directed to a method producing bicyclic guanidine comprising heating a cyclic thiourea to a temperature ranging from $\geq 140°$ C. in a substantially non-hydrocarbon solvent to form the bicyclic guanidine.

16 Claims, No Drawings

METHOD FOR PRODUCING BICYCLIC GUANIDINES BY USE OF A CYCLIC THIOUREA

BACKGROUND OF THE INVENTION

1. Field of the Invention

The present invention relates to a method for producing bicyclic guanidines.

2. Background Information

It is well known that bicyclic guanidines, such as 1,5,7-triazabicyclo[4.4.0]dec-5-ene (TBD) is chemically active and, therefore, can be used to catalyze a variety of chemical reactions. An important consideration in the commercial exploitation of bicyclic guanidines as a catalyst (for any reaction) is that bicyclic guanidines be relatively inexpensive to purchase or easily produced. Published methods for synthesizing bicyclic guanidines, however, are often complicated, often involve the use of a multiple step synthesis process, and/or require the use of prohibitively expensive starting materials which may be hazardous in a variety of ways.

SUMMARY OF THE INVENTION

The present invention is directed to a method producing bicyclic guanidines comprising heating a cyclic thiourea to a temperature $\geq 140°$ C. in a substantially non-hydrocarbon solvent to form the bicyclic guanidines.

DETAILED DESCRIPTION OF THE INVENTION

As used herein, unless otherwise expressly specified, all numbers such as those expressing values, ranges, amounts or percentages may be read as if prefaced by the word "about", even if the term does not expressly appear. Plural encompasses singular and vice versa. For example, although reference is made herein (including the claims) to "an" (aminoalkyl) amine, "a" carbonate, a combination (i.e., a plurality) of (aminoalkyl) amines and/or carbonates may be used.

As used herein, "plurality" means two or more.

As used herein, "includes" and like terms means "including without limitation."

When referring to any numerical range of values, such ranges are understood to include each and every number and/or fraction between the stated range minimum and maximum.

The present invention is directed towards a method of producing bicyclic guanidines. Specifically, the present invention is directed towards a method of producing bicyclic guanidines that comprises heating a cyclic thiourea to a temperature$\geq 140°$ C. in a substantially non-hydrocarbon solvent. It has been surprisingly found that the production of bicyclic guanidines through the process disclosed herein can provide a yield of $\geq 85\%$, such as from 90% to 95%, of the bicyclic guanidine reaction product. Not wishing to be bound by any particular theory, it is believed that the high yield that can be obtained using the disclosed method is due to the fact that a non-hydrocarbon solvent is used during the process of heating the cyclic thiourea.

As stated above, the process disclosed in this invention comprises heating a cyclic thiourea to a temperature$\geq 140°$ C., such as from 140° C. to 250° C. or $\geq 250°$ C., in a substantially non-hydrocarbon solvent in order to form the bicyclic guanidine reaction product. Suitable substantially non-hydrocarbon solvents that may be utilized in the present invention include, without limitation, ethereal solvents as well as alcohols. Suitable ethereal solvents that may be utilized in the present invention include, without limitation, triethlyene glycol dimethyl ether, diethylene glycol dibutyl ether, or combinations thereof. Suitable alcohols that may be utilized in the present invention include, without limitation, ether functional alcohol, butyl carbitol, bisphenol-A, or combinations thereof. In certain embodiments, the ether functional alcohol comprises a glycol ether. Suitable glycol ethers that may be used in the present invention include, without limitation, diethylene glycol monobutyl ether, dipropylene glycol monobutyl ether, or combinations thereof.

In certain embodiments, the cyclic thiourea is formed by reacting an (aminoalkyl) amine with carbon disulfide. As used herein, the term "(aminoalkyl) amine" refers generally to a compound having the formula $H_2N(CR^3R^4)_nNH(CR^5R^6)_mNH_2$ wherein n and m are independently integers having a value in the range from 2 to 6 and wherein $R^3$, $R^4$, $R^5$, and $R^6$ are independently hydrogen or substituted or unsubstitued alkyl or aryl groups. In addition, the composition of each individual $—CR^3R^4—$ and $—CR^5R^6—$ unit may also differ from one another. For example, in certain embodiments the $R^3$ group may comprise $—CH_2—$ while the $R^5$ group may comprise $—CH_2CH_2CH_2—$. Particularly, suitable (aminoalkyl) amines are those where $R^3$, $R^4$, $R^5$, and $R^6$ are independently hydrogen or a $C_1$-$C_3$ alkyl group. Suitable (aminoalkyl) amines within the formula described in this paragraph and which may be used in the present invention include, without limitation, bis(2-aminoethyl)amine, bis(3-aminopropyl)amine, or combinations thereof.

It should be noted that, in certain embodiments, the (aminoalkyl) amine is heated to a temperature of $\geq 100°$ C. prior to the carbon disulfide being added to the (aminoalkyl) amine. Alternatively, in certain embodiments, the carbon disulfide is added to the (aminoalkyl) amine when the (aminoalkyl) amine is at a temperature of $\leq 40°$ C.

In certain embodiments, a catalyst, such as an acid or base catalyst, can be added to the reaction mixture of the (aminoalkyl) amine and the carbonate. Any catalyst known in the art may be used. For example, suitable catalysts include, without limitation, mineral acids, organic acids, Lewis acids, para-toluenesulfonic acid, dimethylaminopyridine, imidazole, TBD, or combinations thereof.

In certain embodiments, the process begins by charging a reaction vessel with the (aminoalkyl) amine and a substantially non-hydrocarbon solvent. In certain embodiments, the non-hydrocarbon solvent is DOWANOL DPnB.

The total amount of carbon disulfide that may be added to the reaction vessel will be dependent upon the total amount of (aminoalkyl) amine that is used in the reaction and can, therefore, be any value, and the rate at which the carbon disulfide is added will be dependent upon the total amount of disulfide that will be added to the reaction vessel. In certain embodiments, the carbon disulfide is added dropwise to the reaction vessel at a rate ranging from 1 grams (g)/minute to 3 g/minute for a total weight ranging from 120 g to 130 g, such as 128 g.

If the carbon disulfide is added to the (aminoalkyl) amine after the (aminoalkyl) amine has been heated to a temperature$\geq 100°$ C., such as 115° C., then a second charge of a substantially hydrocarbon solvent, which can be the same or different from the non-hydrocarbon solvent that was initially charged with the (aminoalkyl) amine, is added to the reaction vessel and the reaction vessel is held at a temperature and for a time period that is sufficient to form the cyclic thiourea and to evolve hydrogen sulfide ($H_2S$) from the reaction vessel. For example, in certain embodiments, the reaction vessel is held at a temperature ranging from 100° C. to 120° C., such as 115° C., for a time period ranging from ≧20 minutes, such as from 30 minutes to 50 minutes.

Alternatively, if the carbon disulfide is added to the (aminoalkyl) amine at a temperature of ≦40° C., such as 25° C., then the reaction vessel is heated to a temperature≧100° C., such as 120° C., for a time period sufficient to completely evolve hydrogen sulfide (H$_2$S) from the reaction vessel. After all the hydrogen sulfide has been evolved from the reaction vessel, a second charge of substantially non-hydrocarbon solvent, which can be the same or different from the non-hydrocarbon solvent that was initially charged with the (aminoalkyl) amine, is added to the reaction vessel and the reaction vessel is held at a temperature and for a time period that is sufficient to form the cyclic thiourea.

After formation of the cyclic thiourea, the cyclic thiourea is heated to a temperature≧140° C., such as 140° C. to 225° C., in order to form the bicyclic guanidine reaction product. In certain embodiments, the cyclic thiourea is heated to a temperature>200° C., such as 220° C. to 240° C. It should be noted that the step of forming the bicyclic guanidine reaction product occurs in the substantially non-hydrocarbon solvent.

After the bicyclic guanidine is formed, it can be isolated by removing the non-hydrocarbon solvent from the reaction vessel. The isolated bicyclic guanidine, which would be in solid form, can then be added to any composition wherein bicyclic guanidine can be used therein. It should also be noted that bicyclic guanidine can also be isolated via precipitation and/or crystallization. Accordingly, in certain embodiments, a solvent, such as heptanes, hexanes, or combinations thereof, is added in which the bicyclic guanidine is insoluble thereby precipitating the bicyclic guanidine.

Alternatively, unisolated bicyclic guanidine may also be admixed with any composition, such as a coating composition, wherein bicyclic guanidine can be used therein. Accordingly, in certain embodiments, the unisolated bicyclic guanidine is cooled to room temperature and a diluent, such as a high-boiling point diluent, is added to the reaction vessel prior to removing the non-hydrocarbon solvent from the reaction vessel. Suitable diluents that may be used in this step include, without limitation, ethoxylated bisphonol A, butyl carbitol formal, or combinations thereof. After removing the non-hydrocarbon solvent from the reaction vessel, the mixture of bicyclic guanidine and diluent may then be admixed with a coating composition, such as an electrodepositable coating composition that is known in the art. For example, in certain embodiments, the bicyclic guanidine formed from the process described herein can be added to the electrodepositable coating composition that is described in U.S. patent application Ser. No. 11/835,600, which is incorporated in its entirety herein by reference.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the claims appended and any and all equivalents thereof.

EXAMPLES

Example 1

A 4 neck flask was equipped with a temperature probe, stainless steel mechanical stirrer, an addition funnel equipped with a Teflon tube for sub-surface addition, and an ice water condenser. Dry nitrogen was swept through the flask, out past the condenser, then through a bump trap and bubbled through a 20% solution of NaOH in water. The flask was charged with DPTA and bisphenol A hexaethoxylate, then warmed to 115° C. The nitrogen flow was reduced so that the reaction was under a pad of inert gas. A solution of carbon disulfide in butyl carbitol formal was added subsurfacely over about 2 hours (h). As the carbon disulfide enters the reaction vessel from the addition funnel, a light colored precipitate was observed to form then quickly redissolve. After complete addition of the CS2, DOWANOL PnB was added dropwise over 15 min, then the reaction mixture was warmed to 225° C. until thiourea intermediate was completely consumed. The hot, homogenous mixture was then cooled, poured out of the reaction vessel, and used without further purification. The concentration of BCG in the final solution was determined by both HPLC and by titration of total base. Typical yields are 80-95% of theory by HPLC and by titration. $^{13}$C NMR analysis indicate that the material consists solely of 1,5,7-triazabicyclo[4.4.0]dec-5-ene in diluents.

Example 2

The process is the same as Example 1, except that during the CS$_2$-butyl carbitol formal mixture the pot temperature is less than 40° C.

What is claimed is:

1. A method for producing bicyclic guanidine comprising heating a cyclic thiourea to a temperature≧140° C. in an ethereal solvent and/or in an alcohol to form the bicyclic guanidine, wherein the cyclic thiourea is the reaction product of (aminoalkyl) amine and carbon disulfide.

2. The method according to claim 1, wherein the carbon disulfide is added to the (aminoalkyl) amine when the (aminoalkyl) amine is at a temperature≧100° C.

3. The method according to claim 1, wherein the carbon disulfide is added to the (aminoalkyl) amine when the (aminoalkyl) amine is at a temperature≦40° C.

4. The method according to claim 1, wherein the reaction between the (aminoalkyl) amine and the carbon disulfide occurs in an ethereal solvent and/or in an alcohol, and wherein the ethereal solvent and/or the alcohol can be the same or different than the ethereal solvent and/or the alcohol used in the step of heating the cyclic thiourea.

5. The method according to claim 1, wherein the temperature is >200° C.

6. The method according to claim 5, wherein the temperature ranges from 220° C. to 250° C.

7. The method according to claim 1, wherein the temperature is ≧250° C.

8. The method according to claim 1, wherein the (aminoalkyl) amine is bis(3-aminopropyl)amine.

9. The method according to claim 1, wherein the ethereal solvent comprises diethylene glycol dimethyl ether, diethylene glycol dibutyl ether, or combinations thereof.

10. The method according to claim 1, wherein the alcohol comprises an ether functional alcohol, butyl carbitol, bisphenol-A, or combinations thereof.

11. The method according to claim 10, wherein the ether functional alcohol comprises a glycol ether.

12. The method according to claim 11, wherein the glycol ether comprises diethylene glycol monobutyl ether, dipropylene glycol monobutyl ether, or combinations thereof.

13. The method according to claim 1, wherein the method further comprises adding a catalyst to the reaction mixture of the (aminoalkyl) amine and the carbon disulfide.

14. The method according to claim 13, wherein the catalyst comprises an acid catalyst.

15. The method according to claim 14, wherein the acid catalyst is para-toluenesulfonic acid.

16. The method according to claim 1, wherein the yield of the bicyclic guanidine is $\geq 80\%$.

* * * * *